(12) United States Patent
Kahn et al.

(10) Patent No.: US 10,791,986 B1
(45) Date of Patent: Oct. 6, 2020

(54) SLEEP SOUND DETECTION SYSTEM AND USE

(71) Applicants: Philippe Kahn, Santa Cruz, CA (US); Arthur Kinsolving, Santa Cruz, CA (US)

(72) Inventors: Philippe Kahn, Santa Cruz, CA (US); Arthur Kinsolving, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

(21) Appl. No.: 13/797,860

(22) Filed: Mar. 12, 2013

Related U.S. Application Data

(60) Provisional application No. 61/620,857, filed on Apr. 5, 2012.

(51) Int. Cl.
*A61B 5/00* (2006.01)
*A61B 5/01* (2006.01)
*A61B 5/0205* (2006.01)
*A61B 5/0476* (2006.01)
*A61B 5/11* (2006.01)
*A61B 7/00* (2006.01)

(52) U.S. Cl.
CPC .......... *A61B 5/4818* (2013.01); *A61B 5/0002* (2013.01); *A61B 5/0077* (2013.01); *A61B 5/01* (2013.01); *A61B 5/02055* (2013.01); *A61B 5/0476* (2013.01); *A61B 5/11* (2013.01); *A61B 5/681* (2013.01); *A61B 5/6803* (2013.01); *A61B 5/6887* (2013.01); *A61B 5/7264* (2013.01); *A61B 5/7275* (2013.01); *A61B 5/742* (2013.01); *A61B 5/746* (2013.01); *A61B 7/003* (2013.01)

(58) Field of Classification Search
CPC ................ A61B 5/4812; A61B 5/4809; A61B 2560/0266; A61B 2560/0475; A61F 5/56; G16H 10/60; G16H 10/65; G06F 19/32; G06F 19/00; G06F 3/165; H04N 21/4424; A61M 2205/52
USPC ........................................................ 600/586
See application file for complete search history.

(56) References Cited

U.S. PATENT DOCUMENTS

| | | |
|---|---|---|
| 3,798,889 A | 3/1974 | Chadwick |
| 4,228,806 A | 10/1980 | Lidow |
| 4,297,685 A | 10/1981 | Brainard, II |
| 4,573,804 A | 3/1986 | Kavoussi et al. |
| 4,788,533 A | 11/1988 | Mequignon |
| 4,848,360 A | 7/1989 | Palsgard et al. |
| 4,858,609 A | 8/1989 | Cole |
| 4,982,738 A | 1/1991 | Griebel |
| 5,008,865 A | 4/1991 | Shaffer et al. |
| 5,275,159 A | 1/1994 | Griebel |
| 5,335,657 A | 8/1994 | Terry, Jr. et al. |

(Continued)

FOREIGN PATENT DOCUMENTS

| | | | |
|---|---|---|---|
| EP | 1139187 B1 | | 10/2001 |
| WO | WO 2008038288 | * | 4/2008 |

*Primary Examiner* — Devin B Henson
*Assistant Examiner* — Huong Q Nguyen
(74) *Attorney, Agent, or Firm* — HIPLegal LLP; Judith Szepesi

(57) ABSTRACT

A method or apparatus comprising monitoring a user's sleep, and turning on a microphone to record sounds, ensuring that the recording occurs in all sleep phases. The method in one embodiment further comprising making the sounds available to the user for later review.

19 Claims, 7 Drawing Sheets

(56) References Cited

U.S. PATENT DOCUMENTS

| | | | |
|---|---|---|---|
| 5,458,105 A * | 10/1995 | Taylor | A61F 5/56 128/848 |
| 5,545,192 A | 8/1996 | Czeisler et al. | |
| 5,562,106 A | 10/1996 | Heeke et al. | |
| 5,671,733 A | 9/1997 | Raviv et al. | |
| 5,844,996 A | 12/1998 | Enzmann et al. | |
| 5,928,133 A | 7/1999 | Halyak | |
| 5,961,447 A | 10/1999 | Raviv et al. | |
| 6,045,514 A | 4/2000 | Raviv et al. | |
| 6,239,706 B1 | 5/2001 | Yoshiike et al. | |
| 6,350,275 B1 | 2/2002 | Vreman et al. | |
| 6,361,508 B1 | 3/2002 | Johnson et al. | |
| 6,468,234 B1 | 10/2002 | Van der Loos et al. | |
| 6,547,728 B1 | 4/2003 | Cornuejols | |
| 6,556,222 B1 | 4/2003 | Narayanaswami | |
| 6,888,779 B2 | 5/2005 | Mollicone et al. | |
| 6,928,031 B1 | 8/2005 | Kanevsky et al. | |
| 6,963,271 B1 | 11/2005 | Fyffe | |
| 7,006,650 B1 | 2/2006 | Wild | |
| 7,106,662 B1 | 9/2006 | Acker | |
| 7,153,278 B2 | 12/2006 | Ono et al. | |
| 7,280,439 B1 | 10/2007 | Shaddox | |
| 7,366,572 B2 | 4/2008 | Heruth et al. | |
| 7,513,003 B2 | 4/2009 | Mossbeck | |
| 7,559,903 B2 | 7/2009 | Moussavi et al. | |
| 7,572,225 B2 * | 8/2009 | Stahmann | A61B 5/00 600/300 |
| 7,841,987 B2 | 11/2010 | Solos et al. | |
| 7,914,468 B2 | 3/2011 | Shalon et al. | |
| 8,179,270 B2 | 5/2012 | Rai et al. | |
| 8,193,941 B2 | 6/2012 | Wolfe et al. | |
| 8,398,546 B2 | 3/2013 | Pacione et al. | |
| 8,407,835 B1 | 4/2013 | Connor | |
| 8,475,339 B2 | 7/2013 | Hwang et al. | |
| 8,482,418 B1 | 7/2013 | Harman | |
| 8,577,448 B2 | 11/2013 | Bauer et al. | |
| 8,680,974 B2 | 3/2014 | Meiertoberens et al. | |
| 8,738,925 B1 | 5/2014 | Park et al. | |
| 8,892,036 B1 | 11/2014 | Causey et al. | |
| 8,942,719 B1 | 1/2015 | Hyde et al. | |
| 9,060,735 B2 | 6/2015 | Yang et al. | |
| 9,161,719 B2 | 10/2015 | Tsutsumi et al. | |
| 9,594,354 B1 | 3/2017 | Kahn et al. | |
| 9,675,268 B2 | 6/2017 | Bauer et al. | |
| 9,844,336 B2 | 12/2017 | Zigel et al. | |
| 10,004,452 B2 | 6/2018 | Kazem-Moussavi et al. | |
| 2002/0080035 A1 | 6/2002 | Youdenko | |
| 2002/0100477 A1 | 8/2002 | Sullivan et al. | |
| 2002/0124848 A1 | 9/2002 | Sullivan et al. | |
| 2003/0095476 A1 | 5/2003 | Mollicone et al. | |
| 2003/0204412 A1 | 10/2003 | Brier | |
| 2003/0231495 A1 | 12/2003 | Searfoss | |
| 2004/0034289 A1 | 2/2004 | Teller et al. | |
| 2004/0049132 A1 | 3/2004 | Barron et al. | |
| 2004/0133081 A1 | 7/2004 | Teller et al. | |
| 2004/0210155 A1 | 10/2004 | Takemura et al. | |
| 2004/0218472 A1 | 11/2004 | Narayanaswami et al. | |
| 2005/0012622 A1 | 1/2005 | Sutton | |
| 2005/0043645 A1 | 2/2005 | Ono et al. | |
| 2005/0075116 A1 | 4/2005 | Laird et al. | |
| 2005/0143617 A1 | 6/2005 | Auphan | |
| 2005/0154330 A1 | 7/2005 | Loree | |
| 2005/0190065 A1 | 9/2005 | Ronnholm | |
| 2005/0236003 A1 | 10/2005 | Meader | |
| 2005/0237479 A1 | 10/2005 | Rose | |
| 2005/0245793 A1 | 11/2005 | Hilton et al. | |
| 2005/0288904 A1 * | 12/2005 | Warrior | H04L 29/06 702/188 |
| 2006/0017560 A1 | 1/2006 | Albert | |
| 2006/0025299 A1 | 2/2006 | Miller et al. | |
| 2006/0064037 A1 | 3/2006 | Shalon et al. | |
| 2006/0097884 A1 * | 5/2006 | Jang | A61B 5/4818 340/575 |
| 2006/0150734 A1 | 7/2006 | Mimnagh-Kelleher et al. | |
| 2006/0252999 A1 | 11/2006 | DeVaul et al. | |
| 2006/0266356 A1 | 11/2006 | Sotos et al. | |
| 2006/0279428 A1 | 12/2006 | Sato et al. | |
| 2006/0293602 A1 | 12/2006 | Clark | |
| 2006/0293608 A1 | 12/2006 | Rothman et al. | |
| 2007/0016091 A1 | 1/2007 | Butt et al. | |
| 2007/0016095 A1 | 1/2007 | Low et al. | |
| 2007/0129644 A1 | 6/2007 | Richards et al. | |
| 2007/0191692 A1 | 8/2007 | Hsu et al. | |
| 2007/0239225 A1 | 10/2007 | Saringer | |
| 2007/0251997 A1 | 11/2007 | Brown et al. | |
| 2007/0287930 A1 | 12/2007 | Sutton | |
| 2008/0062818 A1 | 3/2008 | Plancon et al. | |
| 2008/0109965 A1 | 5/2008 | Mossbeck | |
| 2008/0125820 A1 * | 5/2008 | Stahmann | A61B 5/0031 607/4 |
| 2008/0191885 A1 | 8/2008 | Iv et al. | |
| 2008/0234785 A1 | 9/2008 | Nakayama et al. | |
| 2008/0243014 A1 | 10/2008 | Moussavi et al. | |
| 2008/0289637 A1 | 11/2008 | Wyss | |
| 2008/0319277 A1 | 12/2008 | Bradley | |
| 2009/0030767 A1 | 1/2009 | Morris et al. | |
| 2009/0048540 A1 | 2/2009 | Otto et al. | |
| 2009/0069644 A1 | 3/2009 | Hsu et al. | |
| 2009/0082699 A1 | 3/2009 | Bang et al. | |
| 2009/0094750 A1 | 4/2009 | Oguma et al. | |
| 2009/0105785 A1 | 4/2009 | Wei et al. | |
| 2009/0121826 A1 | 5/2009 | Song et al. | |
| 2009/0128487 A1 | 5/2009 | Langereis et al. | |
| 2009/0143636 A1 | 6/2009 | Mullen et al. | |
| 2009/0177327 A1 | 7/2009 | Turner et al. | |
| 2009/0203970 A1 | 8/2009 | Fukushima et al. | |
| 2009/0207028 A1 | 8/2009 | Kubey et al. | |
| 2009/0227888 A1 * | 9/2009 | Salmi | A61B 5/1118 600/534 |
| 2010/0010330 A1 | 1/2010 | Rankers et al. | |
| 2010/0061596 A1 | 3/2010 | Mostafavi et al. | |
| 2010/0079291 A1 | 4/2010 | Kroll et al. | |
| 2010/0079294 A1 | 4/2010 | Rai et al. | |
| 2010/0083968 A1 | 4/2010 | Wondka et al. | |
| 2010/0094148 A1 | 4/2010 | Bauer et al. | |
| 2010/0100004 A1 | 4/2010 | Someren | |
| 2010/0102971 A1 * | 4/2010 | Virtanen | A61B 5/11 340/575 |
| 2010/0152543 A1 | 6/2010 | Heneghan et al. | |
| 2010/0152546 A1 | 6/2010 | Behan et al. | |
| 2010/0256512 A1 * | 10/2010 | Sullivan | 600/529 |
| 2010/0283618 A1 | 11/2010 | Wolfe et al. | |
| 2010/0331145 A1 | 12/2010 | Lakovic et al. | |
| 2011/0015495 A1 | 1/2011 | Dothie et al. | |
| 2011/0018720 A1 | 1/2011 | Rai et al. | |
| 2011/0058456 A1 | 3/2011 | De et al. | |
| 2011/0090226 A1 | 4/2011 | Sotos et al. | |
| 2011/0105915 A1 | 5/2011 | Bauer et al. | |
| 2011/0137836 A1 | 6/2011 | Kuriyama et al. | |
| 2011/0160619 A1 | 6/2011 | Gabara | |
| 2011/0190594 A1 | 8/2011 | Heit et al. | |
| 2011/0199218 A1 * | 8/2011 | Caldwell | A61B 5/11 340/575 |
| 2011/0230790 A1 | 9/2011 | Kozlov | |
| 2011/0295083 A1 | 12/2011 | Doelling et al. | |
| 2012/0004749 A1 | 1/2012 | Abeyratne et al. | |
| 2012/0083715 A1 | 4/2012 | Yuen et al. | |
| 2012/0232414 A1 | 9/2012 | Mollicone et al. | |
| 2012/0243379 A1 | 9/2012 | Balli | |
| 2012/0253220 A1 | 10/2012 | Rai et al. | |
| 2013/0012836 A1 | 1/2013 | Veiga et al. | |
| 2013/0018284 A1 | 1/2013 | Kahn et al. | |
| 2013/0023214 A1 | 1/2013 | Wang et al. | |
| 2013/0053653 A1 | 2/2013 | Cuddihy et al. | |
| 2013/0053656 A1 | 2/2013 | Mollicone et al. | |
| 2013/0060306 A1 | 3/2013 | Colbauch | |
| 2013/0144190 A1 * | 6/2013 | Bruce | A61B 5/4818 600/586 |
| 2013/0184601 A1 | 7/2013 | Zigel et al. | |
| 2013/0204314 A1 | 8/2013 | Miller et al. | |
| 2013/0208576 A1 | 8/2013 | Loree et al. | |
| 2013/0286793 A1 | 10/2013 | Umamoto | |
| 2013/0289419 A1 | 10/2013 | Berezhnyy et al. | |
| 2013/0310658 A1 | 11/2013 | Ricks et al. | |

(56) References Cited

U.S. PATENT DOCUMENTS

| | | |
|---|---|---|
| 2014/0005502 A1 | 1/2014 | Klap et al. |
| 2014/0051938 A1 | 2/2014 | Goldstein et al. |
| 2014/0135955 A1 | 5/2014 | Burroughs |
| 2014/0171815 A1 | 6/2014 | Yang et al. |
| 2014/0200691 A1 | 7/2014 | Lee et al. |
| 2014/0207292 A1 | 7/2014 | Ramagem et al. |
| 2014/0219064 A1 | 8/2014 | Filipi et al. |
| 2014/0232558 A1 | 8/2014 | Park et al. |
| 2014/0259417 A1 | 9/2014 | Nunn et al. |
| 2014/0276227 A1 | 9/2014 | Perez |
| 2014/0288878 A1 | 9/2014 | Donaldson |
| 2014/0371635 A1 | 12/2014 | Shinar et al. |
| 2015/0068069 A1 | 3/2015 | Tran et al. |
| 2015/0073283 A1 | 3/2015 | Vugt et al. |
| 2015/0098309 A1 | 4/2015 | Adams et al. |
| 2015/0141852 A1 | 5/2015 | Dusanter et al. |
| 2015/0148871 A1 | 5/2015 | Maxik et al. |
| 2015/0173671 A1 | 6/2015 | Paalasmaa et al. |
| 2015/0178362 A1 | 6/2015 | Wheeler |
| 2015/0190086 A1 | 7/2015 | Chan et al. |
| 2015/0233598 A1 | 8/2015 | Shikii et al. |
| 2015/0265903 A1 | 9/2015 | Kolen et al. |
| 2017/0003666 A1 | 1/2017 | Nunn et al. |

\* cited by examiner

SLEEP SOUND DETECTION SYSTEM AND USE

RELATED APPLICATIONS

This patent claims priority to U.S. Provisional Application No. 61/620,857 filed on Apr. 5, 2012, and incorporates that application in its entirety.

FIELD

This patent relates to sleep, and more particularly to sleep sounds.

BACKGROUND

Sleep is sometimes problematic for people. Snoring can be an issue for the snorer, as well as anyone sleeping in their vicinity. There are numerous methods of attempting to cope with snoring.

One prior art method of determining snoring and its cause is sleep studies. Sleep studies involve sleeping numerous nights in a laboratory that monitors the user's snoring, oxygen flow, and other physiological symptoms during sleep. This information can be used to determine when and why someone snores. However, sleep studies are time consuming and expensive, and people's sleep patterns are sometimes disrupted because of the change in environment.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A method or apparatus to track, and in one embodiment reduce, user snoring and/or other unhealthy sleep behaviors is described. Snoring may be an indication of health issues, such as sleep apnea, and generally is correlated with less restful sleep. Furthermore, snoring can disturb the sleep of others. There are many variations of snoring. While loud snorers are often aware of their snoring, intermittent snorers or those who sleep alone may not be aware that they are snoring. In addition to snoring, the sleep sound system may be able to detect, and recommend corrective action for, teeth grinding, restless leg syndrome, sleep apnea (disrupted breathing), and other conditions that may be identified based on sensor and sound data recorded during the user's sleep.

The present system uses a sleep monitoring mechanism, in conjunction with a microphone or other mechanism to monitor a user's sleep sounds. The sleep sounds can then be analyzed, and data may be used to inform the user and/or appropriate other party such as a medical provider, make recommendations, and/or for other purposes. In one embodiment, the audio data may also be used in determining the user's sleep state. In one embodiment, the audio data may be recorded, so that an appropriate professional may evaluate it.

The following detailed description of embodiments of the invention make reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims.

Figure 1:
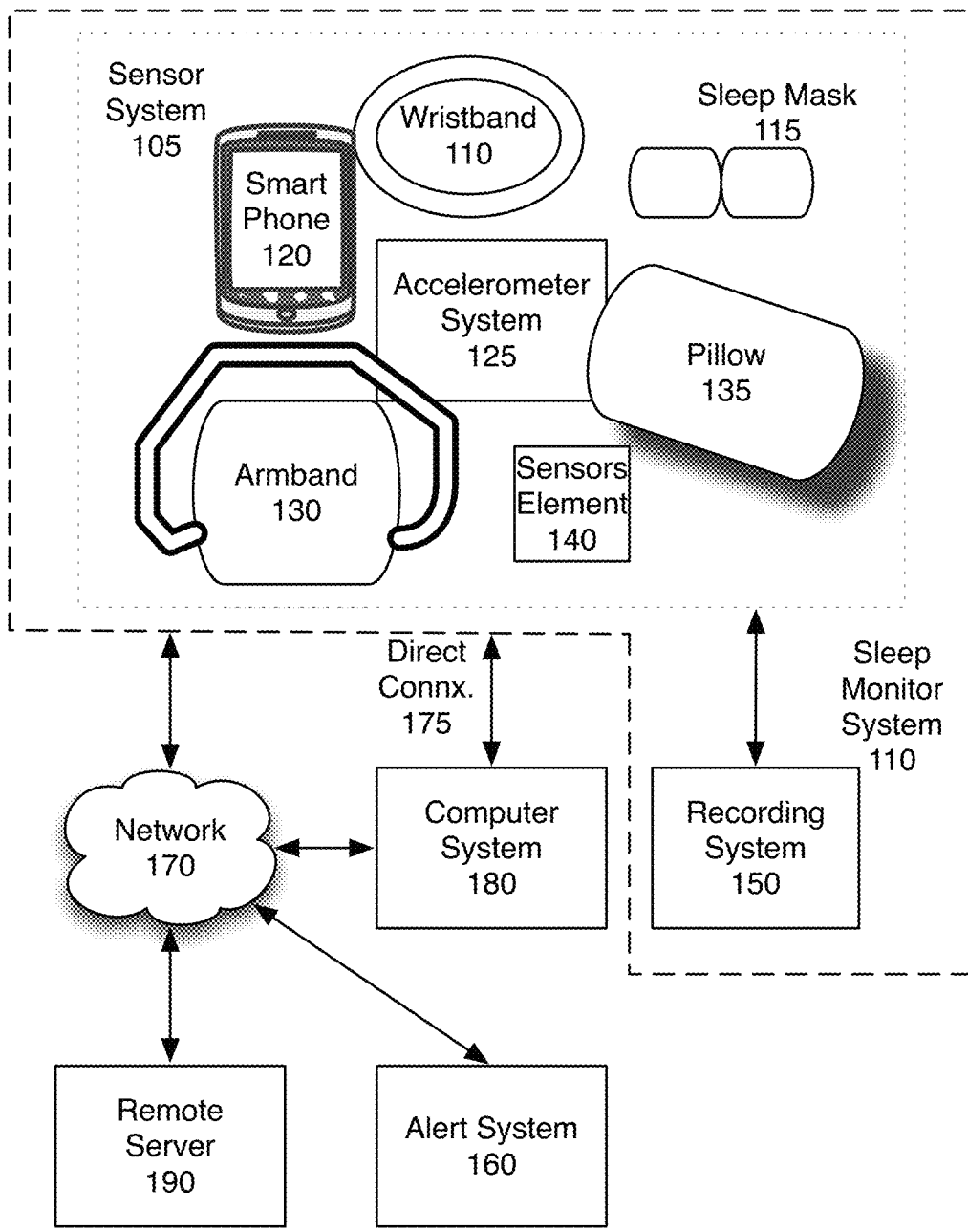
FIG. 1 is a block diagram of a network in which the present invention may be used.

FIG. 1 is a block diagram of a network in which the present invention may be used. The sleep monitor system 110 may be coupled to a computer system 180 either directly or via a network 170. In one embodiment, the sleep monitor system 110 may be coupled to an external alert system 160 either directly or via a network 170. The sleep monitor system 110 may also be coupled to a remote server 190 via network 170. The network 170 may be a wireless network, such as Wi-Fi, a cellular network, a personal area network such as Bluetooth, or another type of network.

In one embodiment, sleep monitor system 110 includes sensor system 105 and recording system 150. Sensor system 105 incorporates one or more sensors, to detect the user's sleep conditions, and recording system 150 utilizes a microphone or video recording to store the user's snoring or other sleep behavior for later analysis.

In one embodiment, sensor system 105's sensors may be incorporated into various formats such as a smart phone 120, wrist band 110, sleep mask 115, pillow 135, armband 135, or other sensor element 140. The system may include a plurality of such devices, each providing one or more sensors. In one embodiment, recording system 150 may also be incorporated into these devices. In another embodiment, the recording system 150 may be separated. If the recording system 150 is a separate system, it may communicate with sensor system 105 via a direct connection or a wireless connection.

Figure 2:
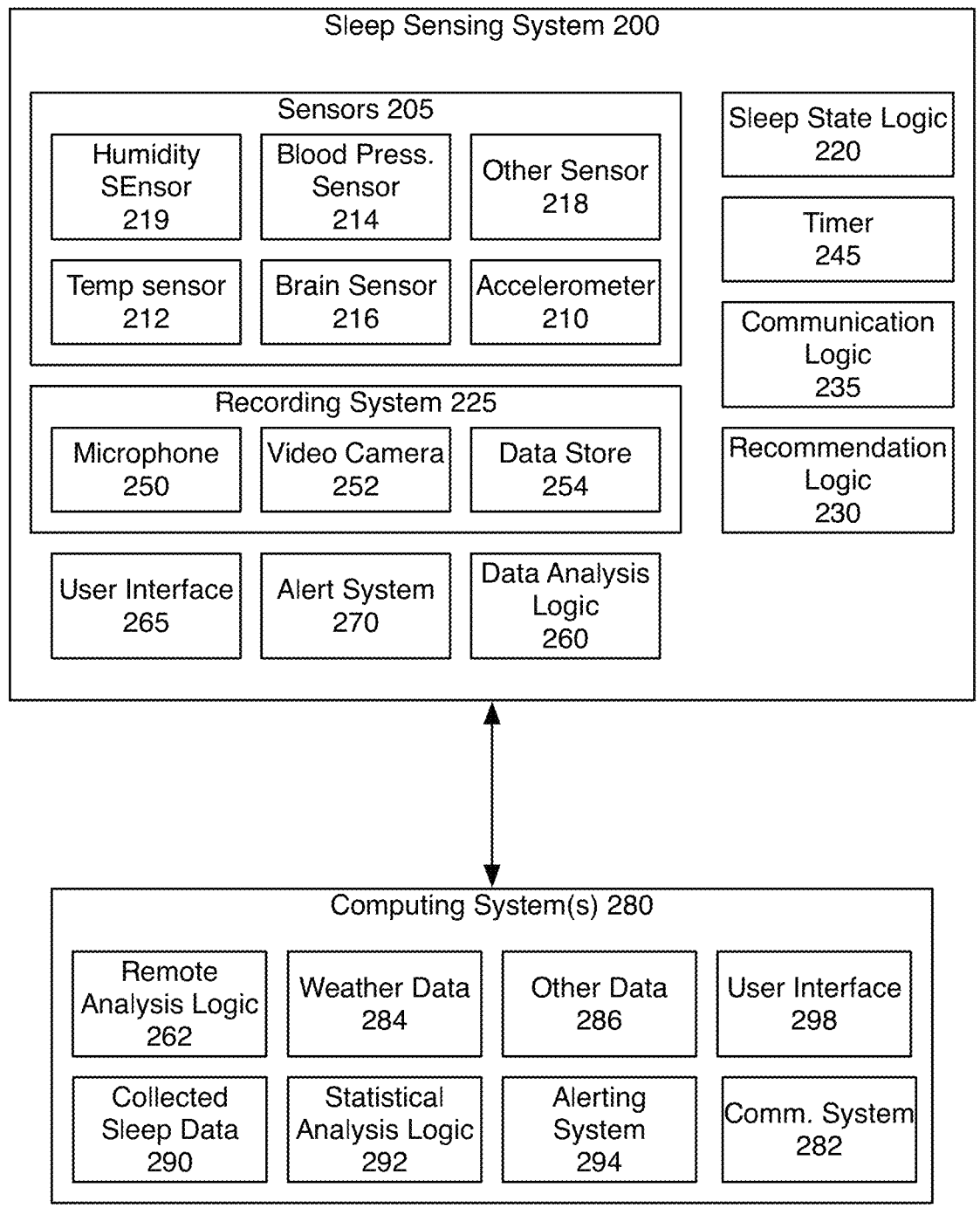
FIG. 2 is a block diagram of one embodiment of the sleep monitoring system.

FIG. 2 is a block diagram of one embodiment of the sleep monitoring system. The sleep sensing system 200 includes a plurality of sensors 205.

The sensors 205, in one embodiment, include motion sensor 210. In one embodiment, motion sensor is an accelerometer 210, used to detect user motion. User motion can be used to determine a user's current sleep phase, as well other aspects of the user's quality of sleep. In one embodiment, sensors 205 may include additional sensors, which may also be used to assist in determining a current sleep phase, as well as to collect relevant data. For example, additional sensors may include one or more of: temperature sensor 212 which may include a body thermometer and/or an ambient temperature thermometer, humidity detector 219, blood pressure monitor 214 brain sensor 216 to detect brain waves which indicate sleep phase, and/or other sensors 218.

The sleep sensing system 200 also includes recording system 225 in one embodiment. The recording system 225 includes a microphone 250, or other sound pick-up mechanism. The microphone 250 is used to pick up sounds, such as the sounds of snoring. In one embodiment, timer 245 controls when microphone 250 is turned on. In one embodiment, the microphone 250 is turned on periodically. In one embodiment, the periodicity is per sleep phase, ensuring that sounds are monitored in each sleep cycle. In one embodiment, the timer 245 is controlled by the sleep state logic 220, which determines the current sleep state based on the sensor data. For example, the recording may be initiated when the data indicates that a sleep state transition has occurred, and periodically thereafter. In one embodiment, a video camera 252 may be turned on when the sleep transition has occurred, or when snoring is detected, etc. In another embodiment, the recording (audio and/or video) may be continuous. The data from the recording system 225 is stored in data store 254. In one embodiment, data store 254 includes the recording data, and correlated sensor data and sleep state information.

Timer 245 may also control when other sensors 205 are turned on.

The sensor data and recording data is recorded in data store 254. In one embodiment, the data is analyzed by data analysis logic 260. Data analysis logic 260 determines whether the sound recorded is that of snoring, in one embodiment. In one embodiment, data analysis logic 260 may also identify recording of other sounds or video that may be indicators of health concern. For example, hick-ups, choking sounds, thrashing, or any other such sounds or movements indicative of a problem. In one embodiment, the data store 254 stores any such relevant data.

In one embodiment, the data store 254 may store continuously recorded sounds/video/sensor data, and may purge "uninteresting" data in a First In-First Out type of system. For example, in one embodiment the data store 254 may allocate two hours worth of audio/video data for a night. Every hour, the recorded data may be analyzed by data analysis logic 260, and when the data is not informative (e.g. no change is occurring, the sleeper continues to sleep in the same sleep phase, the snoring continues at the same volume and intensity, etc.) the data may be discarded.

In one embodiment, data analysis logic 260 can be used to assist in diagnosing and treating various conditions. Over time, the data analysis logic 260, or statistical analysis logic 292, monitor data and build up information about what variables/conditions effect the person's conditions for the better and worse. This data can be used by the user, medical personnel, or an appropriate other party to help understand what makes various conditions better and worse. In one embodiment, recommendation logic 230 can provide information based on this information, to recommend adjustments in the user's behavior and environment/conditions. This applies to snoring, choking, or any of other conditions. Recommendation logic 230 may output its recommendations via communication logic 235.

The user interface system 265 allows display of the recorded data. In one embodiment, the recorded data may actually be displayed on the user interface 298 on computer system 280 when the data from sleep monitor system 200 is sent to the computer system 280.

In one embodiment, for certain high-risk sounds detected, the data analysis logic 260 may send the data to alert system 270. Alert system 270 may be a local speaker or other output mechanism, the user's mobile telephone number, a doctor or other relevant contact, or similar destination. In one embodiment, for choking or other sounds that may indicate immediate health distress, alert system 270 or UI system 265 may attempt to waken the user immediately.

In one embodiment, the data from sleep monitor system 200 may be sent to a computer system 280, either directly or via a network, such as a wireless network. The computing system 280 may be a local device or a server system. In one embodiment, the computer system 280 may perform the data analysis, using remote data analysis logic 262, and return data to the sleep monitor system 200, via communication system 282, to communication logic 235. In one embodiment, data analysis logic 260 and remote analysis logic 262 may share processing, such that some, or all, of the more processing-intensive analysis is done remotely.

In one embodiment, the computer system 280 may receive statistical data from the sleep monitoring system 200, and collect such abstracted data from a large number of users, as collected sleep data 290. This enables statistical analysis logic 292 to perform cumulative data analysis to determine risk factors for snoring or other adverse health events across anonymized data from many users. For example, the system may determine that certain users snore more, and have less restful sleep, when the temperature is above 76 degrees Fahrenheit. This may enable the system, via UI 265 or UI 298 to suggest to a user to reduce the bedroom temperature.

In one embodiment, the computer system 280 may utilize additional data, such as weather data 284 or other data 286, in addition to sensor data received, to form a more complete picture of the environment. For example, local weather data 284 obtained from third party sources, may be added to the sensor data received from various users.

Figure 3:
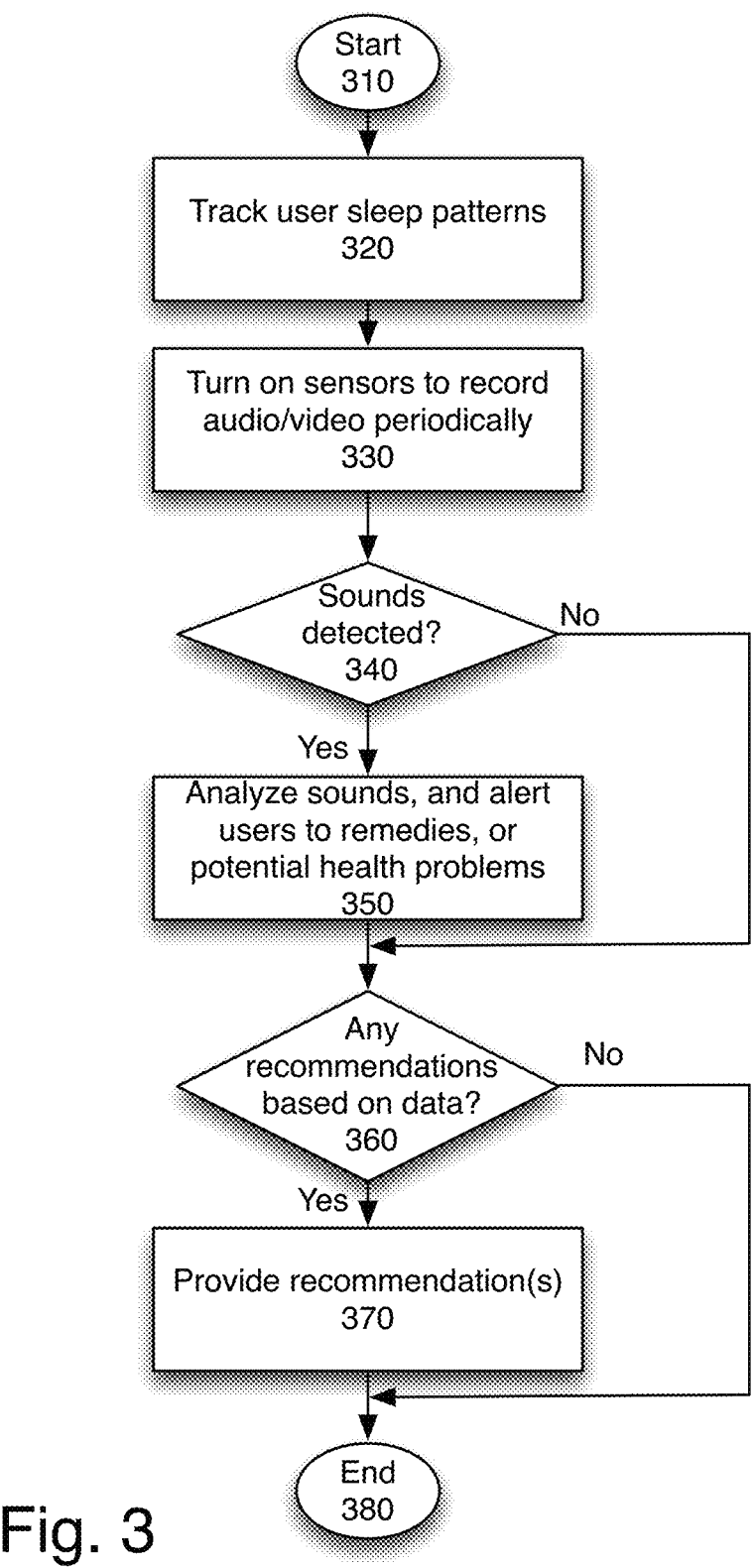
FIG. 3 is an overview flowchart of one embodiment of monitoring the sleep.

FIG. 3 is an overview flowchart of one embodiment of monitoring sleep. The process starts at block 310. In one embodiment, the process is initiated when the user indicates that he or she is going to sleep. In one embodiment, this may be done through selecting a "sleep" option, or interacting with the sleep sensing system in some way, e.g. laying down on the pillow, wearing the mask, wearing the arm band, placing the wristband/armband/smart phone into sleep mode, etc. In another embodiment, the user falling asleep may be automatically detected.

At block 320, the process tracks the user's sleep patterns. The sleep tracking may occur through motion tracking, as with an accelerometer, through cameras, and/or other sensors. In one embodiment, the data from the combination of sensors may be used. Sleep tracking may categorize the user's current sleep by phase, e.g. deep sleep, light sleep, awake, or optionally N1, N2, N3, and deep sleep, or using another pattern. The user's sleep patterns, in one embodiment, are divided up into sleep phases. In one embodiment, a plurality of sensors' data may be combined to determine the sleep phases.

At block 330, the process periodically turns on the microphone to record the sounds being made by the sleeper. In one embodiment, the periodicity is designed to ensure that the microphone is turned for some time on during all phases of sleep. In one embodiment, the system may also periodically turn on a video camera or take still images. In one embodiment, the recording may be turned on based on the user's sleep state, as determined by the sensors in the sleep monitor. In one embodiment, the recording may be turned on periodically. In another embodiment, the recording may be continuous. In another embodiment, when other sensor data indicates snoring, or distress, the recording may be turned on.

Figure 4:
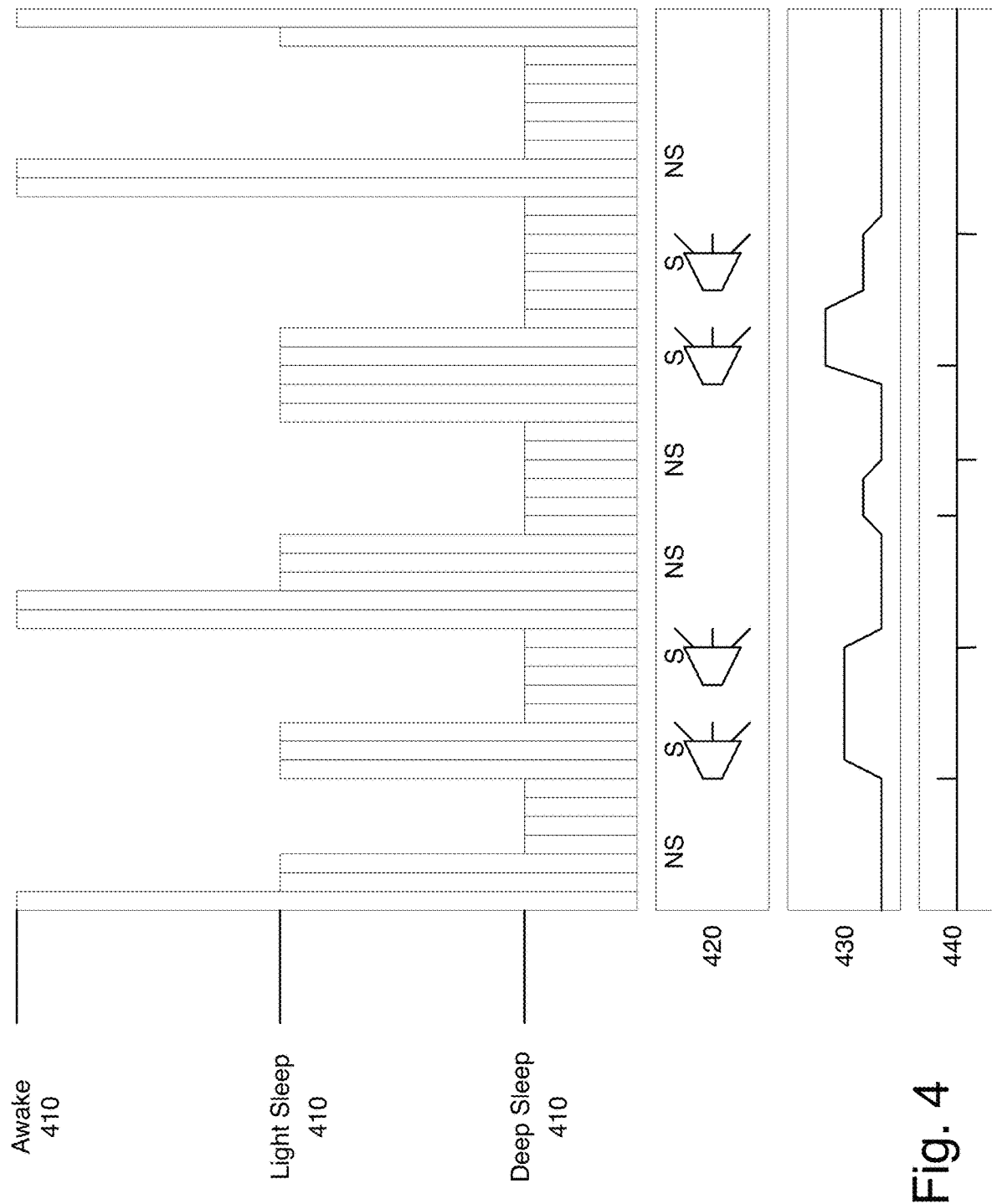
FIG. 4 is a figure illustrating one embodiment of displaying the information.

FIG. 4 illustrates an exemplary user interface display for the sleep data including the snoring data. In one embodiment, the various phases of sleep are indicated 410, with the snoring data, or absence of snoring data, indicated via icons along an indicator 420. Here, it can be seen that the NS indicates "no snoring detected" while S indicates snoring. In one embodiment, the recorded snoring may be available for replay, to the user or to a relevant professional. In another embodiment, the data may be captured continuously, with an indication of snoring levels, as show in indicator 430. In another embodiment, meta-tags may be added to indicate where along the timeline snoring is found, as shown in indicator 440. Alternate methods of indicating the relevant sleep sounds may be utilized.

Returning to FIG. 3, at block 340, the process determines whether any snoring was detected. In one embodiment, this process is performed on a computer system, when the data is moved to the computer system. In another embodiment, this processing may be done in the sleep monitor system. In one embodiment, it may be done continuously, periodically, or at the end of each sleep period. If no snoring was detected, the process ends at block 360.

If snoring was detected, at block 350, the snoring is analyzed, and the snoring data is made available to the user. In one embodiment, the snoring data may be associated with the sleep quality data, which may be available to the user.

At block 360, the process determines whether based on the monitored data, there are any recommendations for adjustments to user behavior and/or environment. For example, the system may determine that the user snores more when the user goes to sleep after midnight. The system may then have a recommendation to reduce snoring. Conditions ranging from activity level, time to bed, light levels in the room, temperatures, or other behaviors or environmental conditions If there are recommendations, at block 370 the recommendation is provided. The recommendation may be provided to the user, an appropriate third party such as a medical professional.

The process then ends at block 380. In one embodiment, if the snoring detected indicates a likely health problem, such as sleep apnea or similar, the user may be sent an alert in addition to making the snoring data available via a user interface. The alert may be a text message, an email, or another mechanism.

Figure 5:
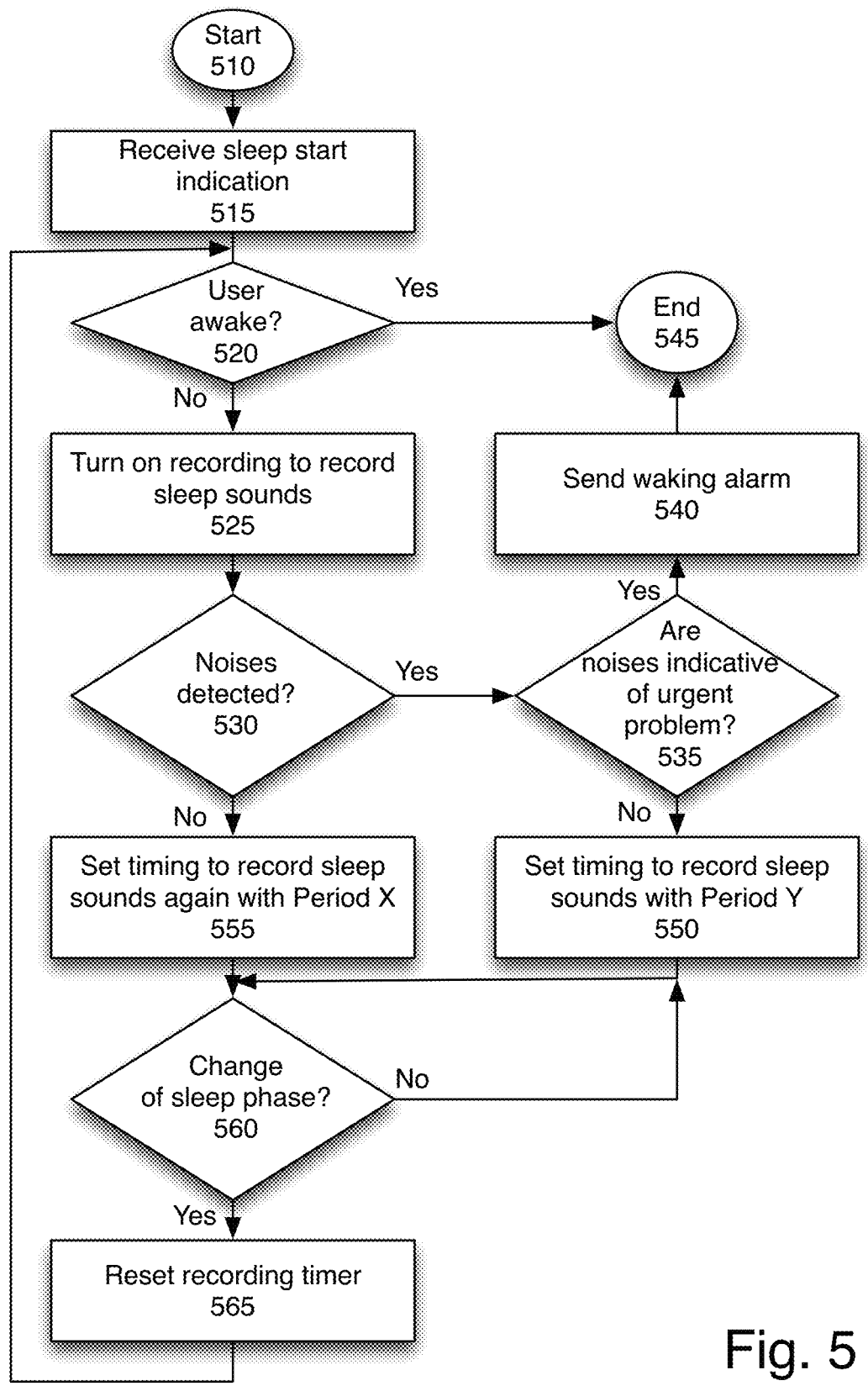
FIG. 5 is a flowchart of one embodiment of detecting snoring.

FIG. 5 is a flowchart of one embodiment of detecting snoring. The process starts at block 510.

At block 515, the user's sleep indication is received. In one embodiment, this may be a manual switch or button used to indicate that the user is going to sleep. In one embodiment, this may be automatically detected by the sleep monitoring system.

At block 520, the process determines whether the user is awake. If the user is awake, e.g. ending the sleep period, the process ends at block 545. In one embodiment, this occurs when the user manually indicates that he or she has finished sleeping. In one embodiment, this may be automatically detected when the user rises from bed or otherwise takes an action that is incompatible with sleep.

If the user is not waking up, at block 525, the recording is turned on to record sleep sounds. In one embodiment, this occurs a set period after the user's sleep is initiated. In another embodiment, the timing of the sound recording may depend on user characteristics. In another embodiment, this may be continuous when the user is sleeping. The recording may be an audio recording, or an audio/visual recording.

At block 530, the process determines whether sleep sounds were detected. These sleep sounds include sounds of snoring, or other noises made by sleeping humans, as well as other noises in one embodiment. If sounds were detected, the process continues to block 535.

At block 535, the process determines whether the noises and/or other data indicate an urgent problem. Such noises may include choking, coughing, fire alarm, or other noises which generally would need a prompt response. If the noises, in one embodiment in combination with other sensor data, are indicative of such an urgent problem, at block 540, a waking alarm is sent to the user. This is designed to wake the user and may be auditory, visual, tactile, or other alarm formats. In one embodiment, the alarm may be sounded directly by the sleep system, sent to a mobile telephone or landline telephone, or otherwise conveyed to the user. In one embodiment, the alarm may also be sent to a third party, when appropriate. The third party may be designed by the user, e.g. the user's partner, medical provider, alarm company, 911 provider, etc. The process then ends, when the user is awakened, at block 545.

If the noises are not indicative of an urgent problem, the process continues to block 550, and the timing to record sleep sounds is set to a period. For example, if snoring is detected, the sleep sounds may be set to record every 15 minutes. In one embodiment, the timing may range from continuous (e.g. 0 seconds), to timing (every 15 minutes), to once per sleep phase, once per sleep cycle, once per sleep time, or even less frequently. The process then continues to block 560.

If at block 530 no noises were detected, at block 555 the timer is set to record sleep sounds with a period. In one embodiment, this period is different from the period set when snoring or other relevant sounds were detected. In one embodiment, the testing for noise is less frequent if no noise was detected. The process then continues to block 560.

At block 560, the process determines whether the sleep phase of the user has changed. In one embodiment, the sleep phase is determined based on data from one or more sensors. In one embodiment, the sleep sounds may be included in making this determination. In general, snoring differs by sleep phase, for most sleepers. Therefore, in one embodiment, the frequency of recording is determined for each sleep phase. If there is no change in sleep phase, the process continues to block 560, to continue recording sleep noises with the periodicity indicated. In one embodiment, any time a sleep sound is detected, the process of verifying that the noise does not require urgent response is applied.

If the sleep phase changes, at block 560, in one embodiment the process resets the recording timer, at block 565. The process then continues to block 520, to determine whether the user is awake.

In one embodiment, the above process is applicable when the system does not have significant amount of data about the user. In one embodiment, once the user's sleep has been monitored over an extended period and no snoring has been detected, the system may set a testing rate for future sleep cycles, without evaluating the detection of noises. In one embodiment, however, if noises are detected, the timing of the testing is adjusted.

Figure 6:
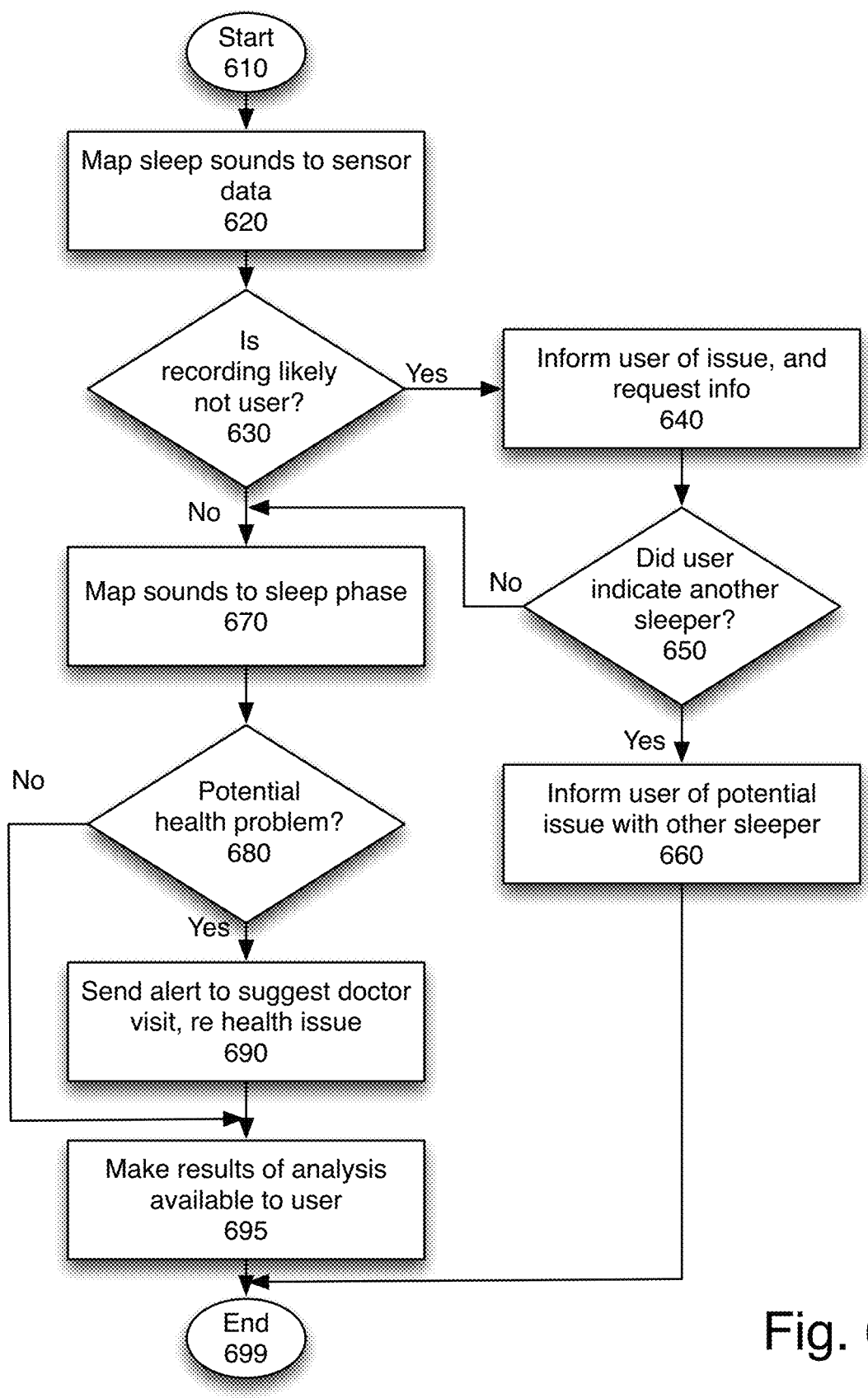
FIG. 6 is a flowchart of one embodiment of analyzing sleep sound data.

FIG. 6 is a flowchart of one embodiment of analyzing snoring data. The process starts at block 610. In one embodiment, this process occurs in a computer system. In one embodiment, this process occurs continuously while the user's sleep is monitored. In another embodiment, this process occurs periodically, when sufficient user data has been accumulated.

At block 620, the snoring is mapped to sensor data. As noted above, the sensor data may include motion data, temperature, video or image data, brainwave data, blood pressure data, heart rate data, etc. In one embodiment, the combination of sensor data is evaluated. In another embodiment, the motion data is evaluated.

At block 630, the process determines whether the recorded sound is likely not the user. In one embodiment, snoring has a somewhat characteristic motion associated with it, e.g. there is a vibration. There may also be an associated brainwave or other sensor data. If the sound has no vibration at all, it is possible that the sound is actually another person in the same room or another room snoring, or a different source.

If the sound is likely not the user, at block 640 the user is informed of the issue, and information is requested about the presence of potentially other snorers or sources of similar sound in the household. If the user indicates, at block 650, that there are no other sleepers or other noise sources, the process continues to block 670. If there is another sleeper, the user is informed of the potential issue with the snoring of the other person, at block 660. The process then ends at block 699.

If the mapping indicated, at block 630, that the user was the likely snorer, the process continues directly to block 670.

At block 670, the snoring data is mapped to the sleep phase in which it occurs. There may be a correlation between snoring timing and potential health issues.

At block 680, the process determines whether the snoring indicates a potential health problem. This may be based on the frequency, loudness, type, or timing of the snoring. If there is a potential health problem, at block 690 an alert is sent to the user, ton suggest following up this issue. At block 695, the results of the analysis are made available to the user. In one embodiment, in addition to alerting the user, a third party may be alerted as well. For example, a medical professional or other relevant party, as indicated by the sleep system. In one embodiment, the user is prompted to enter additional information, when available. For example, if an alert is sent, suggesting a visit to a doctor, a follow-up may ask whether the user did visit a doctor, and results of that visit.

If there is no potential health problem indicated, at block 680, the process continues to block 695, to make the results of the analysis available to the user. An anonymized version of this information may be passed to the server, and used in future analysis of sleep issues in a cumulative manner, in one embodiment. For example, if the recommendation for a doctor visit results in the use of a sleep aid, a tool for preventing grinding of teeth, or medication, this information may be used to refine future recommendations regarding potential health problems. The process ends at block 699.

While the above process is described with respect to snoring, one of skill in the art would understand that the same combination of movement and periodic sound recording data may be used to analyze for teeth grinding, sleep walking, wheezing, or other potentially harmful health indicators which may be observed during sleep. In one embodiment, sleep sounds are useful as a feedback loop, to provide audio data that the user or a healthcare provider may listen to, and evaluate for problems. The sleep sound data may also be used as sensor data, to determine sleep phase, as well as sleep quality.

One of skill in the art would understand that although the above description is with respect to sleep sounds, a similar logic may be applied in recording video, brain data, imaging data, or other types of sensor data that could provide useful information about a user's sleep and/or health.

Figure 7:
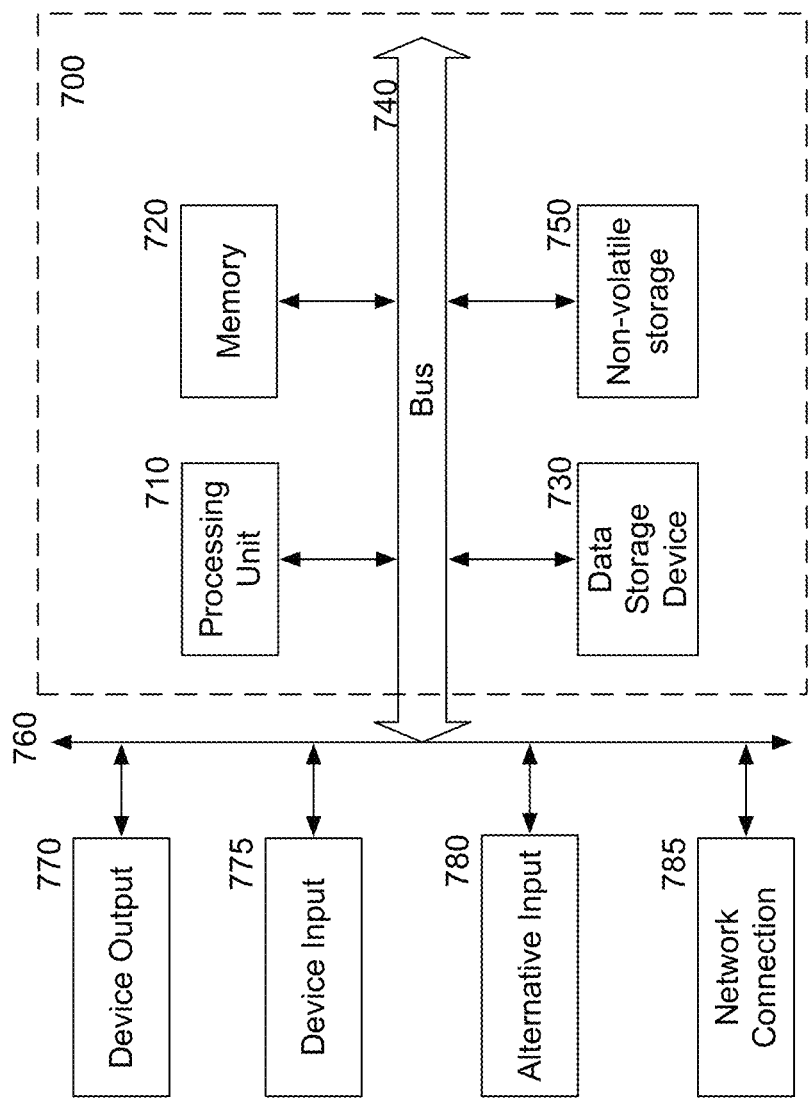
FIG. 7 is a block diagram of one embodiment of a computer system with which the present invention may be used.

FIG. 7 is a block diagram of one embodiment of a computer system with which the present invention may be used. FIG. 7 is a block diagram of a particular machine, which may be used with the present invention. It will be apparent to those of ordinary skill in the art, however that other alternative systems of various system architectures may also be used.

The data processing system illustrated in FIG. 7 includes a bus or other internal communication means 740 for communicating information, and a processing unit 710 coupled to the bus 740 for processing information. The processing unit 710 may be a central processing unit (CPU), a digital signal processor (DSP), or another type of processing unit 710.

The system further includes, in one embodiment, a random access memory (RAM) or other volatile storage device 720 (referred to as memory), coupled to bus 740 for storing information and instructions to be executed by processor 710. Main memory 720 may also be used for storing temporary variables or other intermediate information during execution of instructions by processing unit 710.

The system also comprises in one embodiment a read only memory (ROM) 750 and/or static storage device 750 coupled to bus 740 for storing static information and instructions for processor 710. In one embodiment, the system also includes data storage device 730 such as a magnetic disk or optical disk and its corresponding disk drive, or Flash memory or other storage, which is capable of storing data when no power is supplied to the system. Data storage device 730 in one embodiment is coupled to bus 740 for storing information and instructions.

The system may further be coupled to an output device 770, such as a cathode ray tube (CRT) or a liquid crystal display (LCD) coupled to bus 740 through bus 760 for outputting information. The output device 770 may be a visual output device, an audio output device, and/or tactile output device (e.g. vibrations, etc.)

An input device 775 may be coupled to the bus 760. The input device 775 may be an alphanumeric input device, such as a keyboard including alphanumeric and other keys, for enabling a user to communicate information and command selections to processing unit 710. An additional user input device 780 may further be included. One such user input device 780 is cursor control device 780, such as a mouse, a trackball, stylus, cursor direction keys, or touch screen, may be coupled to bus 740 through bus 760 for communicating direction information and command selections to processing unit 710, and for controlling movement on display device 770.

Another device, which may optionally be coupled to computer system 700, is a network device 785 for accessing other nodes of a distributed system via a network. The communication device 785 may include any of a number of commercially available networking peripheral devices such as those used for coupling to an Ethernet, token ring, Internet, or wide area network, personal area network, wireless network, or other method of accessing other devices. The communication device 785 may further be a null-modem connection, or any other mechanism that provides connectivity between the computer system 700 and the outside world.

Note that any or all of the components of this system illustrated in FIG. 7 and associated hardware may be used in various embodiments of the present invention.

It will be appreciated by those of ordinary skill in the art that the particular machine which embodies the present invention may be configured in various ways according to the particular implementation. The control logic or software implementing the present invention can be stored in main memory 720, mass storage device 730, or other storage medium locally or remotely accessible to processor 710.

It will be apparent to those of ordinary skill in the art that the system, method, and process described herein can be implemented as software stored in main memory 720 or read only memory 750 and executed by processor 710. This control logic or software may also be resident on an article of manufacture comprising a computer readable medium having computer readable program code embodied therein and being readable by the mass storage device 730 and for causing the processor 710 to operate in accordance with the methods and teachings herein.

The present invention may also be embodied in a handheld or portable device containing a subset of the computer hardware components described above. For example, the handheld device may be configured to contain only the bus 740, the processor 710, and memory 750 and/or 720.

The handheld device may be configured to include a set of buttons or input signaling components with which a user may select from a set of available options. These could be considered input device #1 775 or input device #2 780. The handheld device may also be configured to include an output device 770 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processing unit 710, a data storage device 730, a bus 740, and memory 720, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 785.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 710. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical, or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A method of improving sleep quality comprising:
   receiving data signifying when a user falls asleep;
   sending a signal to a sleep monitoring system to automatically monitor the user's sleep, the sleep monitoring system including one or more sensors and a processor configured to identify sleep phases of the user based on sensor data from the one or more sensors;
   detecting the user's sleep sounds;
   sending a signal to create an audio recording of at least a subset of the user's sleep sounds periodically during the user's sleep such that the recording is not continuous, the recording using a microphone;
   storing the audio recording of the subset of the user's sleep sounds in a memory;
   identifying a first portion of the audio recording in the memory that is not informative of sleep quality, wherein the first portion of the audio recording is identified as not informative when no change is occurring in the user's sleep sounds and no change is occurring in the sleep phase from sleep sounds recorded prior to the first portion of the audio recording;
   discarding the first portion of the audio recording that is not informative of sleep quality from the memory, to create relevant sleep sound data of the user from a remainder of the audio recording, wherein the remainder of the audio recording is limited to an allocated length of time in the memory;
   generating sleep analysis data, based on correlating a timeline of the relevant sleep sound data from the remainder of the audio recording with a timeline of sleep phase data and sleep time data;
   receiving and storing in the memory the sleep analysis data, for later review.

2. The method of claim 1, further comprising:
   determining if the user's sleep sounds of the remainder of the audio recording indicates an issue; and
   sending a signal configured to wake the user when the user's sleep sounds of the remainder of the audio recording indicates the issue.

3. The method of claim 1, wherein the sleep monitoring system comprises one or more of: a smart phone, a wristband, an armband, a pillow, a sleep mask, and an accelerometer system.

4. The method of claim 1, further comprising:
   said sending a signal to create the audio recording of at least the subset of the user's sleep sounds is sent in response to receiving, at the processor, at least one of: the sleep phase, the user's sleep sounds previously recorded, and a likelihood of snoring.

5. The method of claim 1, further comprising:
   analyzing the relevant sleep sound data to determine whether a potential health condition is indicated; and
   sending a signal configured to inform the user of the potential health condition.

6. The method of claim 1, wherein the subset of the user's sleep sounds comprise one or more of: snoring, teeth grinding, interrupted breathing, gasping for air, coughing.

7. The method of claim 1, wherein:
a length of the audio recording of the subset of the user's sleep sounds created periodically is shorter when no noise is detected and longer when snoring or other sounds are detected.

8. The method of claim 1, further comprising:
displaying a sleep record to the user, the sleep record displayed as a timeline showing the sleep phases and indicators along the timeline indicating the user's sleep sounds.

9. A smart phone, including a processor, the smart phone used as a sleep monitoring system comprising:
one or more sensors configured to monitor a user's sleep and to provide sensor data to the processor, the sensor data representing the user's sleep;
a recording system, including a microphone, the recording system configured to periodically record the user's sleep sounds during the user's sleep in all sleep phases, a length of a period to record the user's sleep sounds set by the sensor data from the one or more sensors, the sleep phases identified based on the sensor data from the one or more sensors;
a memory configured to:
store in a data store the user's sleep sounds and a time and the sleep phase for the user's sleep sounds, for later review;
the processor, to cause the memory to store a first recorded length of the user's sleep sounds that is informative of sleep quality for the user, in the data store, and discard from the data store a second recorded length of the user's sleep sounds that is not informative, wherein the second recorded length is identified as not informative when no change is occurring in the user's sleep sounds and no change is occurring in the sleep phase, compared to the first recorded length of the user's sleep sounds,
wherein the first recorded length of the user's sleep sounds is limited to an allocated length of time in the memory; and
the processor further to correlate a timeline of the first recorded length of the user's sleep sounds that is informative of sleep quality for the user with a timeline of the sensor data provided by the one or more sensors; and
a user interface configured to present at least the sensor data from the one or more sensors to the user.

10. The sleep monitoring system of claim 9, further comprising:
a data analysis logic configured to, when executed by the processor, determine if the first recorded length of the user's sleep sounds that is informative of sleep quality for the user indicate an issue; and
an alert system including a speaker, the alert system configured to wake the user when the first recorded length of the user's sleep sounds indicate the issue.

11. The sleep monitoring system of claim 9, wherein the length of the period depends on one or more of: a current sleep phase, the user's sleep sounds previously recorded, and a likelihood of snoring.

12. The sleep monitoring system of claim 9, wherein the memory is further configured to:
store a data analysis logic configured to, when executed by the processor, analyze the first recorded length of the user's sleep sounds to determine whether a potential health condition is indicated by the combination of the user's sleep sounds that is informative of sleep quality and the sensor data; and
wherein the user interface is configured send a signal to inform the user of the potential health condition.

13. The sleep monitoring system of claim 9, wherein the user's sleep sounds comprise one or more of: snoring, teeth grinding, interrupted breathing, gasping for air, coughing.

14. The sleep monitoring system of claim 9, wherein the memory is further configured to:
store a data analysis logic configured to, when executed by the processor, correlate the timeline of the first recorded length of the user's sleep sounds that is informative of sleep quality with the timeline of the sensor data from the one or more sensors, resulting in a time-correlated data; and
store the time-correlated data.

15. The sleep monitoring system of claim 14, wherein the user interface is configured to receive instructions to display a sleep record to the user, the sleep record including information on the sleep phase and the first recorded length of the user's sleep sounds that is informative of sleep quality.

16. A sleep quality improvement system comprising:
a sensor system including one or more sensors to output sensor data and configured to monitor a user's sleep;
a recording system including a microphone and a processor, the recording system configured to periodically record into a memory the user's sleep sounds during the user's sleep in all sleep phases, and further configured to receive a periodic signal to begin the recording, a length of a period between the periodic signals based on the sensor data from the one or more sensors;
a computer system configured to receive a signal to remotely store and analyze the recorded user's sleep sounds, as correlated with the sensor data, and determine if a recorded non-snoring sleep sound indicates an issue;
an alert system including a speaker,
the memory including computer instructions to determine whether the recorded non-snoring user's sleep sound indicates the issue,
the processor being configured to determine whether the recorded non-snoring user's sleep sound indicates the issue, and to output a signal configured to wake the user when the recorded non-snoring user's sleep sound indicates the issue, using the alert system; and
the processor configured to execute a data analysis logic to discard from the memory a first portion of the periodically recorded user's sleep sounds when the first portion of the user's sleep sounds are not informative, wherein the first portion of the user's sleep sounds are identified as not informative when no change is occurring in the user's sleep sounds and no change is occurring in the user's sleep phase, compared to sleep sounds recorded prior to the first portion, wherein a remaining portion of the recorded user's sleep sounds is limited to an allocated length of time in the memory;
a user interface to provide the sensor data from the one or more sensors and the recording system to the user.

17. The sleep monitoring system of claim 16, wherein the sensor system further includes at least one of: a smart phone, a wristband, an armband, a pillow, a sleep mask, and an accelerometer system.

18. The sleep monitoring system of claim 16, further comprising:
a sleep sensing system which includes at least one of: humidity sensor; blood pressure sensor; temperature sensor; brain wave sensor; and accelerometer system.

19. A method of improving sleep quality comprising:
receiving data signifying when a user falls asleep;

sending a signal to a sleep monitoring system to automatically monitor the user's sleep, the sleep monitoring system including one or more sensors and a processor configured to identify sleep phases of the user based on sensor data from the one or more sensors;

sending a signal to a microphone to record at least a subset of the user's sleep sounds periodically during the user's sleep such that recording is not continuous and such that a length of the period to record the user's sleep sounds is based on the sensor data from the one or more sensors, and the recording occurring in all of the sleep phases;

further comprising:

storing the periodically recorded user's sleep sounds in a memory;

periodically during the user's sleep, identifying a first portion of the periodically recorded user's sleep sounds as not informative when no change is occurring in the user's sleep sounds and no change is occurring in the sleep phase, compared to sleep sounds recorded prior to the first portion;

discarding the first portion of the periodically recorded user's sleep sounds that is not informative of sleep quality from the memory to create relevant sleep data of the user from a remainder of the periodically recorded user's sleep sounds, wherein sleep sounds for each sleep phase in the remainder of the periodically recorded user's sleep sounds are retained, and a total length of the remainder of the periodically recorded user's sleep sounds are time limited to an allocated length of time in the memory;

receiving the sensor data from the one or more sensors, the sensor data including both time data and sleep-phase data;

sending the time data from the one or more sensors, and the sleep-phase data, over a network to be remotely converted into sleep analysis data;

receiving and storing in the memory the remotely converted sleep analysis data, for later review; and correlating, at the processor, a timeline of the remotely converted sleep analysis data and a timeline of the relevant sleep data to produce time-correlated data.

\* \* \* \* \*